(12) United States Patent  
Bruinsma et al.

(10) Patent No.: US 8,547,551 B2  
(45) Date of Patent: Oct. 1, 2013

(54) LITHOGRAPHIC APPARATUS AND CONTAMINATION DETECTION METHOD

(75) Inventors: Anastasius Jacobus Anicetus Bruinsma, Delft (NL); Johannes Hubertus Josephina Moors, Helmond (NL); Lucas Henricus Johannes Stevens, Eindhoven (NL); Abraham Veefkind, Noordwijk (NL); Peter Gerhardus Wihelmus Bussink, 's-Gravenhage (NL); Egbert Anne Martijn Brouwer, Zoetermeer (NL)

(73) Assignee: ASML Netherlands B.V., Veldhoven (NL)

( * ) Notice: Subject to any disclaimer, the term of this patent is extended or adjusted under 35 U.S.C. 154(b) by 336 days.

(21) Appl. No.: 12/935,786

(22) PCT Filed: Mar. 27, 2009

(86) PCT No.: PCT/NL2009/050151  
§ 371 (c)(1),  
(2), (4) Date: Dec. 9, 2010

(87) PCT Pub. No.: WO2009/123446  
PCT Pub. Date: Oct. 8, 2009

(65) Prior Publication Data  
US 2011/0090495 A1    Apr. 21, 2011

Related U.S. Application Data

(60) Provisional application No. 61/064,889, filed on Apr. 1, 2008.

(51) Int. Cl.  
*G01J 4/00* (2006.01)

(52) U.S. Cl.  
USPC .......................................................... 356/364

(58) Field of Classification Search  
USPC .......................................................... 356/364  
See application file for complete search history.

(56) References Cited

U.S. PATENT DOCUMENTS

| | | | | |
|---|---|---|---|---|
| 5,748,318 | A | * | 5/1998 | Maris et al. .................... 356/630 |
| 6,891,627 | B1 | | 5/2005 | Levy et al. ..................... 356/625 |

(Continued)

FOREIGN PATENT DOCUMENTS

TW    200745537    12/2007

OTHER PUBLICATIONS

International Search Report as issued for PCT/NL2009/050151, dated Jun. 22, 2009.

(Continued)

*Primary Examiner* — Tarifur Chowdhury  
*Assistant Examiner* — Omar Nixon  
(74) *Attorney, Agent, or Firm* — Pillsbury Winthrop Shaw Pittman LLP

(57) ABSTRACT

A lithographic apparatus includes a vessel that encloses a component with a test surface to be probed for contamination control; and an optical probe configured to transmit and receive an optical probing beam. The vessel includes a first optical port configured to transfer the optical probing beam towards the test surface, and a second optical port configured to receive a reflected optical probing beam. The optical probe includes a light source configured to provide the optical probing beam, a polarization conditioner configured to provide a predefined polarization state to the probing beam, and a spectral analyzer. The polarization conditioner is preset to provide a minimal transmission for a minimal transmission wavelength, and the spectral analyzer is arranged to detect a wavelength shift of the minimal transmission wavelength in response to a polarization change due to the presence of contamination.

15 Claims, 8 Drawing Sheets

(56) References Cited

U.S. PATENT DOCUMENTS

| | | | |
|---|---|---|---|
| 7,342,235 B1 * | 3/2008 | Harrison et al. | 250/372 |
| 2006/0067606 A1 * | 3/2006 | Towle et al. | 385/14 |
| 2007/0139646 A1 | 6/2007 | Singh | 356/237.2 |
| 2007/0146657 A1 | 6/2007 | Mierlo et al. | 355/30 |

OTHER PUBLICATIONS

Chinese Office Action dated Feb. 25, 2013 in corresponding Chinese Patent Application No. 200980110569.0.

* cited by examiner

LITHOGRAPHIC APPARATUS AND CONTAMINATION DETECTION METHOD

CROSS-REFERENCE TO RELATED APPLICATIONS

This application claims the benefit of U.S. provisional application 61/064,889, which was filed on Apr. 1, 2008, and which is incorporated herein in its entirety by reference.

FIELD

The present invention relates to a lithographic apparatus and a method for detecting contamination within a lithographic apparatus.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

While contamination control is an issue for any lithographic apparatus, including conventional transmissive lens based systems, and especially for systems generally referenced as EUV (Extreme UltraViolet) systems, operating on shorter wavelengths operating below 20 nm, contamination control of mirror systems is desirable due to the sources that have a challenging contamination control. Reflection of EUV radiation uses specific mirror design with advanced materials. The reflectivity of these mirrors influences the EUV transmission of this imaging system. The interaction of EUV light with CxHy molecules at or near the surface of these mirrors causes deposition of carbon at the mirror surface. The latter significantly affects the reflective properties of the mirrors and thus it affects the EUV transmission of the imaging optical system.

SUMMARY

While monitoring systems are known to observe the contamination growth in EUV systems, a desire still exists to provide a monitoring tool that has a robust service level in operating conditions, especially in (vacuum) closed confinements.

According to an aspect of the invention, there is provided a lithographic apparatus that includes a vessel that encloses a component with a test surface to be probed for contamination control, and an optical probe configured to transmit and receive an optical probing beam. The vessel includes a first optical port configured to transfer the optical probing beam towards the test surface, and a second optical port configured to receive a reflected optical probing beam. The optical probe includes a light source configured to provide the optical probing beam, a polarization conditioner configured to provide a predefined polarization state to the probing beam, and a spectral analyzer. The polarization conditioner is preset to provide a minimal transmission for a minimal transmission wavelength. The spectral analyzer is arranged to detect a wavelength shift of the minimal transmission wavelength in response to a polarization change due to the presence of contamination.

According to an aspect of the invention, there is provided a vessel enclosing a component with a test surface to be probed for material deposition control, and an optical probe configured to transmit and receive an optical probing beam. The vessel includes a first optical port configured to transfer the probing beam towards the test surface, and a second optical port configured to receive a reflected probing beam. The optical probe includes a broadband light source configured to provide the probing beam, a polarization conditioner to provide a predefined polarization state to the probing beam, a polarization filter, and a spectral analyzer, the polarization conditioner and polarization filter being preset to provide a null transmission for a predefined minimal transmission wavelength, and the spectral analyzer being arranged to detect a wavelength shift of the minimal transmission wavelength in response to a polarization change due to the presence of contamination.

According to an aspect of the invention, there is provided a contamination monitoring method for monitoring contamination of a test surface enclosed in a vessel. The method includes transmitting an optical probing beam into the vessel, conditioning the optical probing beam to provide a minimal transmission after reflection on the test surface for a predefined minimal transmission wavelength and polarization state, receiving a reflected optical probing beam from the vessel into a spectral analyzer, and detecting a wavelength shift of the minimal transmission wavelength in response to a polarization change due to the presence of contamination with the spectral analyzer.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
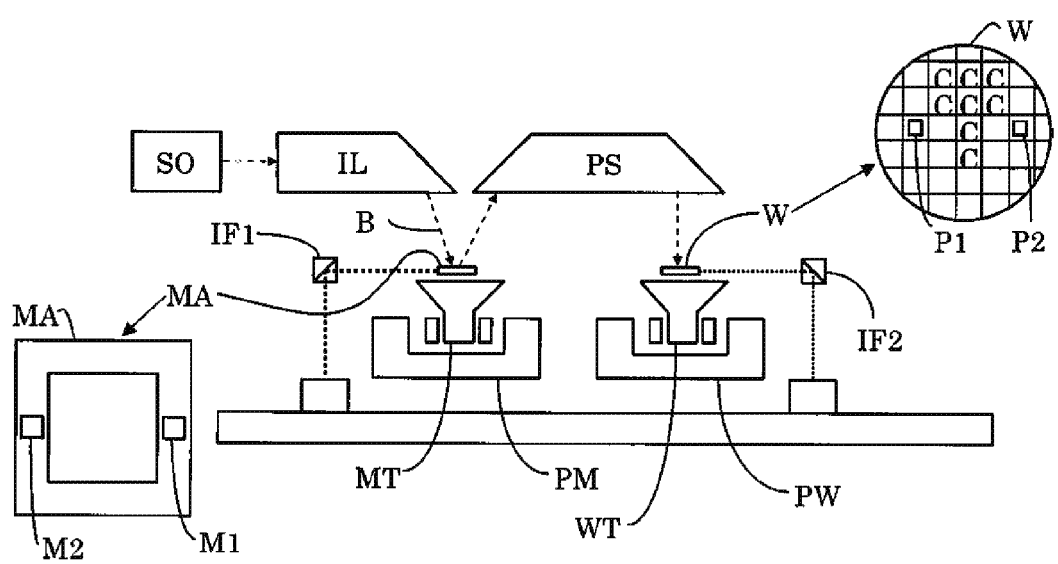
FIG. 1 depicts a lithographic apparatus according to an embodiment of the invention.

FIG. 1 schematically depicts a lithographic apparatus according to one embodiment of the invention. The apparatus comprises: an illumination system (illuminator) IL configured to condition a radiation beam B (e.g. UV radiation or EUV radiation); a support structure (e.g. a mask table) MT constructed to support a patterning device (e.g. a mask) MA and connected to a first positioner PM configured to accurately position the patterning device in accordance with certain parameters; a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PS configured to project a pattern imparted to the radiation beam B by patterning device MA onto a target portion C (e.g. comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a reflective type (e.g. employing a reflective mask). Alternatively, the apparatus may be of a transmissive type (e.g. employing a transmissive mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system comprising, for example, suitable directing mirrors and/or a beam expander. In other cases the source may be an integral part of the lithographic apparatus, for example when the source is a mercury lamp. The source SO and the illuminator IL, together with the beam delivery system if used, may be referred to as a radiation system.

The illuminator IL may comprise an adjuster for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator and a condenser. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PS, which focuses the beam onto a target portion C of the substrate W. With the aid of the second positioner PW and position sensor IF2 (e.g. an interferometric device, linear encoder or capacitive sensor), the substrate table WT can be moved accurately, e.g. so as to position different target portions C in the path of the radiation beam B. Similarly, the first positioner PM and another position sensor IF1 can be used to accurately position the mask MA with respect to the path of the radiation beam B, e.g. after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e. a single dynamic exposure). The velocity and direction of the substrate table WT relative to the mask table MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
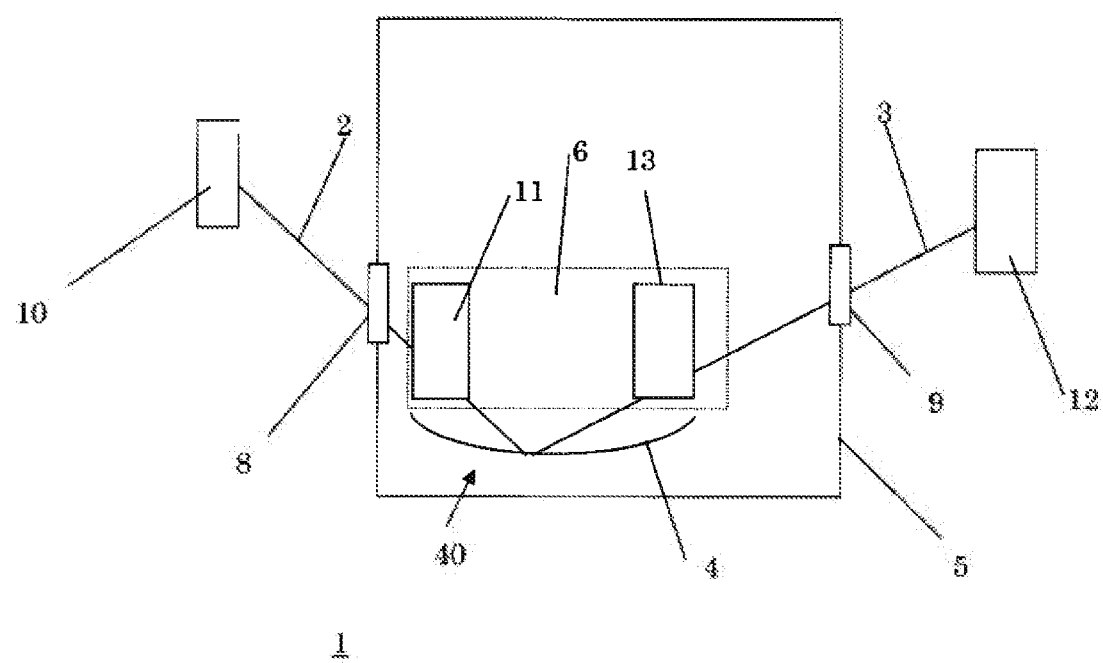
FIG. 2 depicts a schematic embodiment of a monitoring device of the lithographic apparatus of FIG. 1.

Ellipsometric methods are known for detecting thin layers of material due to changed reflective properties of a surface 4 (See FIG. 2). Generally, the polarization state of a probing beam 2 is altered after reflection. It is known that for different polarizations, reflection coefficients are different. These coefficients can be calculated using the Fresnel equations. If the light is polarized with the electric field of the light perpendicular to the plane of the diagram above (s-polarized), the reflection coefficient is given by:

$$R_s = \left[\frac{\sin(\theta_t - \theta_i)}{\sin(\theta_t + \theta_i)}\right]^2 = \left[\frac{n_1 \cos(\theta_i) - n_2 \cos(\theta_t)}{n_1 \cos(\theta_i) + n_2 \cos(\theta_t)}\right]^2 \quad (1)$$

where $\theta_t$ (angle of reflection) can be derived from $\theta_i$ (angle of incidence) by Snell's law.

If the incident light is polarized in the plane of the diagram (p-polarized), the reflection coefficient is given by:

$$R_p = \left[\frac{\tan(\theta_t - \theta_i)}{\tan(\theta_t + \theta_i)}\right]^2 = \left[\frac{n_1 \cos(\theta_t) - n_2 \cos(\theta_t)}{n_1 \cos(\theta_t) + n_2 \cos(\theta_t)}\right]^2 \quad (2)$$

The ratio of equations (1) and (2) gives rise to the fundamental equation in ellipsometry:

$$\rho = \frac{r_p}{r_s} = \tan(\Psi) e^{i\Delta} \quad (3)$$

Thus, tan $\Psi$ is the amplitude ratio upon reflection, and $\Delta$ is the phase shift (difference).

By providing an input beam of a predefined (elliptical) polarization state, the reflected beam can be linearized depending on the reflective properties of the reflector. Null ellipsometry is thus used to tune the probing beam so that the reflectance is linearly polarized, so that the transmittance of the ellipsometer becomes zero for a predefined wavelength.

In order to provide the predefined polarization state and analyze the reflected beam, conventional ellipsometers are massive systems using moving and rotating parts. These systems are therefore not suitable for application in vacuum or in highly clean areas as well as in confined areas, such as a vessel.

FIG. 2 shows an embodiment of a monitoring device in a lithographic apparatus 1, wherein a small passive ellipsometer 6 is provided based on the (known) null ellipsometry concept. Accordingly, in a lithographic apparatus 1 a vessel 5 is provided. Typically, the vessel 5 can be a vacuum vessel, although the embodiments of the method is applicable in any confined area which is difficult to reach or which is preferably kept in operation conditions at all times. One example is a transmissive lens system housing. Another example is the projection system of an EUV lithographic system, housing a plurality of projective optics, in particular, reflective elements for imaging an EUV image. This housing is also referenced as a projection optics box. Another example is the illuminator system for transferring the EUV radiation to the patterning device or reticle. Typically, accordingly, a component 40 is confined in the vessel 5, which, due to operating conditions, has a test surface 4 that is to be probed for contamination control. This component 40 is thus typically a projection optic, such as a reflective mirror, that is to be kept clean for optimal imaging conditions. Examples of contamination are carbon, zinc, tin oxide and tin droplets.

An optical probing system or optical probe is formed by source 10, polarization conditioning system or polarization conditioner 11, a polarization filter 13 and spectral analyzer 12. The source 10 emits an optical probing beam 2 into the vessel 5 via a optical port 8. The optical port 8 transfers the probing beam 2 towards the test surface 4. After reflection, another optical port 9 receives a reflected probing beam 3.

The source 10 may be a broadband light source, in a specific example, this may be a tunable wavelength source. Although in general null elipsometry a single wavelength may be used, according to embodiments of the method, by using a broadband light, a wavelength shift can be detected of the wavelength that has zero transmittance. This may have an advantage that no optical adjustment is necessary but a preset optical polarization can be used. To that end, the polarization conditioning system 11 is provided. The polarization conditioning system 11 provides a predefined polarization state to the probing beam—for all wavelengths, the light is conditioned to have a predefined (complex) polarization vector preset to provide a linear polarizion state after reflection at test surface 4, thus providing a null transmission through polarization filter 13 for a predefined wavelength, called the minimal transmission wavelength. Due to the presence of vacuum within the vessel 5, the polarization conditioning system 11 may be provided within the vessel to prevent optical distortion at the vacuum interface of the optical ports 8, 9. Thus, the broadband light source is light guided into the vessel via the optical port, for example, by optical fibers; and the reflected light beam is guided, after passing polarization filter 13, towards spectral analyzer 12, which may be provided outside the vessel 5.

Spectral measurement of the light that is detected by analyzer 12 provides a spectral response curve with a distinct minimum. The position of this minimum in the total measured spectral range can be tuned by adjusting the optical elements of the polarization conditioning system 11 and the orientation of polarization filter 13.

After reflection, and while using a polarization filter 13 and a spectral analyzer 12, a wavelength shift of said minimum can be detected in response to a polarization change due to the presence of contamination.

Figure 3:
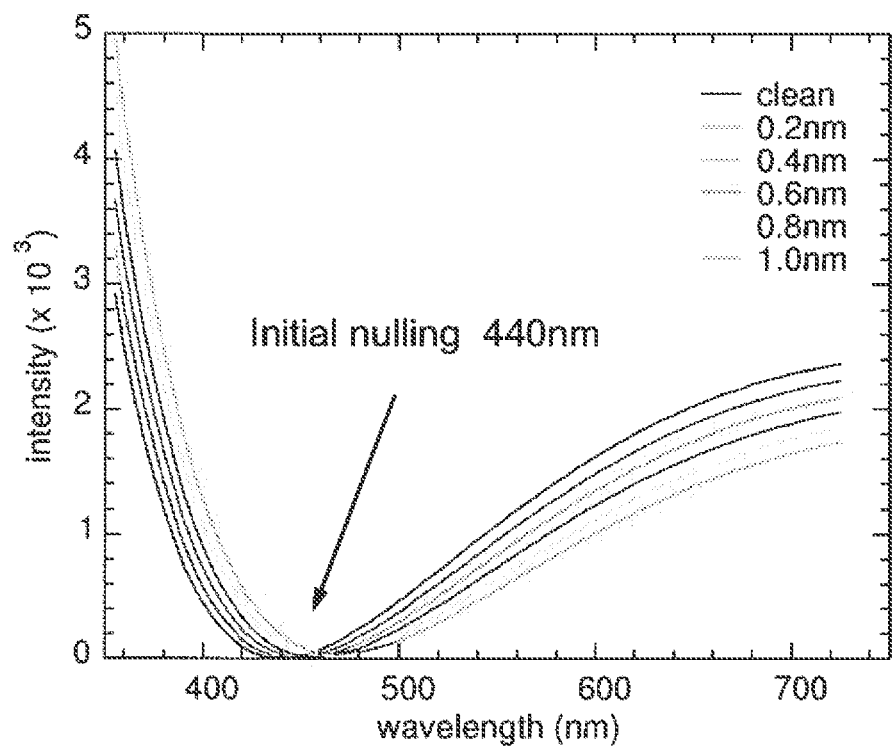
FIG. 3 depicts a spectral response for different carbon layer thicknesses.

FIG. 3 shows that a change of the carbon layer thickness at the surface 4 of the test mirror results in a shift of the position of the minimum along the measured spectral range. The position of this minimum can be assessed by signal processing software arranged in the spectral analyzer 12. Accordingly, the spectral analyzer, or a computer connected thereto, is arranged with minimum identifying circuitry for identifying a local minimum in the received wavelength spectrum, and a memory for associating a local minimum shift to a contamination level. The minimum identifying circuitry uses well-known computational methods, such as Newton-Rapson methods or similar methods. In principle, the proposed measurement concept may distinguish between carbon growth and other accumulated molecules at the surface of the mirror due to different spectral signatures of these materials. Examples are Zn, Tin oxide and Tin molecules.

Figure 4:
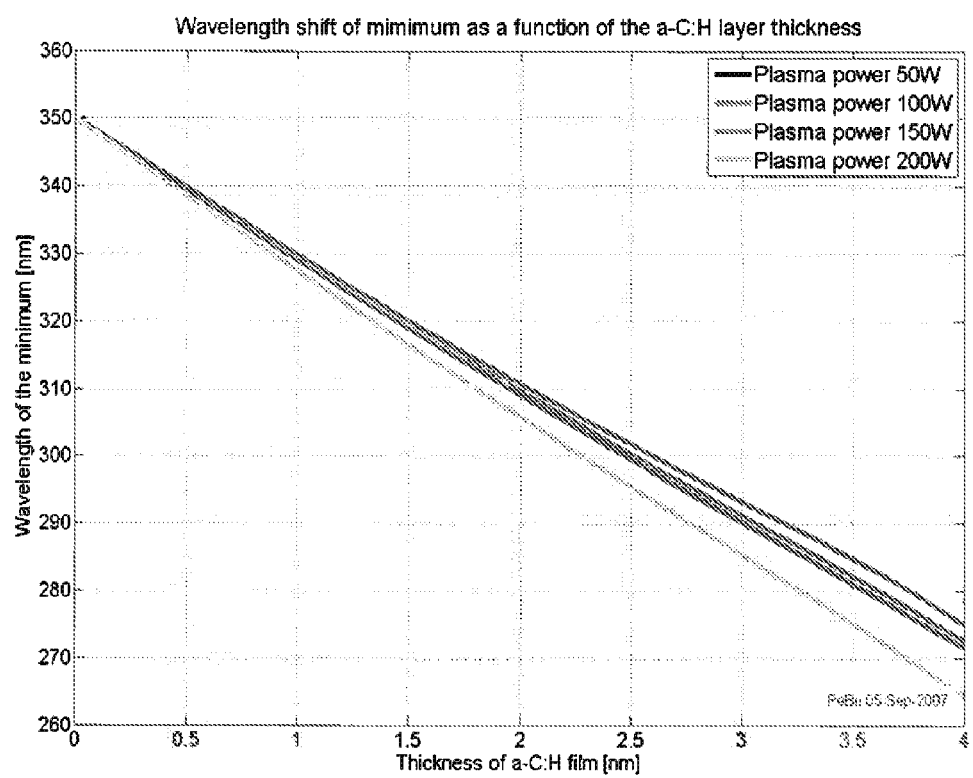
FIG. 4 depicts a wavelength shift of the minimum transmission wavelength as a function of the carbon layer thickness.

FIG. 4 shows that the wavelength shift as a function of carbon layer thickness is close to linear in the layer thickness range of 0 to 4 nm.

Various practical implementations of the concept are possible which enable a compact sensor and which dramatically simplify the integration of the sensor in the complex mechanical structure of the projection optics box (EUV optical imaging system) or EUV illuminating system. Another example of such an implementation is provided in FIG. 5.

This compact embodiment only uses a single optical port 8, due to the provision of a retroreflective element or retroreflector 15 arranged in a beam path of the probing beams (2,3). The retroreflective element 15 is positioned to direct the reflected probing beam 3 via the test surface 4 from and to the optical port 8. Additionally, by reflecting twice with the test surface, the sensitivity can be enhanced. The passive null ellipsometer 6 is much smaller and less expensive than well-known ellipsometers. In addition, integration in the optical imaging system may be considerably simplified.

Figure 5:
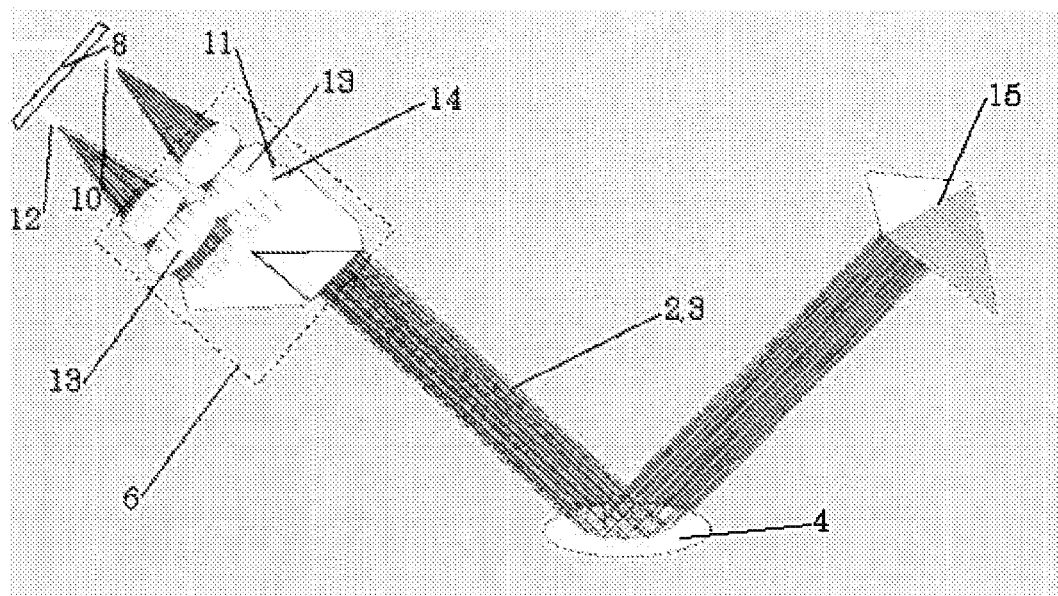
FIG. 5 depicts an embodiment of the monitoring device.

The embodiment of FIG. 5 further shows that the polarization conditioning system 11 may comprise a polarizer 13 (a polarizing or polarization filter) and a retarder 14, such as a quarter waveplate.

Typically, the polarization conditioning system 11 is provided, in an optical path from the broadband light source 10, with a polarizer 13 and a retarder 14. A polarization filter 13 is arranged in the optical path between the optical port before the spectral analyzer 12. The polarization filter 13 can null this beam. Accordingly, for a minimal transmission wavelength, a polarization condition can be provided to the probing beam to render a linear polarization to the reflective beam 3, which can be nulled. When the reflective conditions of the reflective test surface 4 change under the influence of contamination growth, the linear polarization will change in another polarization condition due to the Ψ (Phi) and Δ (Delta) values of the fundamental equation (3) discussed above FIG. 6 shows an embodiment of the retroreflector 15. According to the embodiment of FIG. 6, the probed light beam 3 travels from test surface 4 to the retroreflector 15 and back. The retroreflector 15 includes a collimating lens 18, a micro lens array 19, and a mirror 20.

Figure 6:
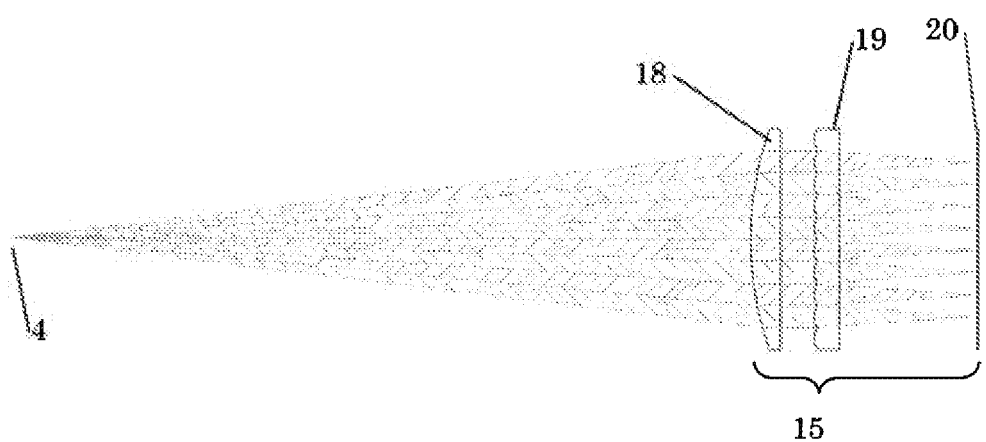
FIG. 6 depicts an embodiment of a retroreflective element of the monitoring device of FIG. 5.
Figure 7:
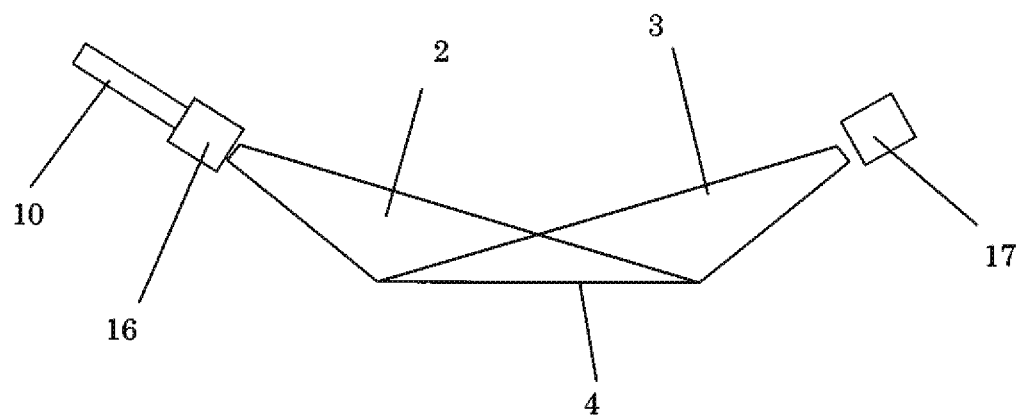
FIG. 7 depicts a side schematic view of an embodiment of an ellipsometric setup for the monitoring device.
Figure 8:
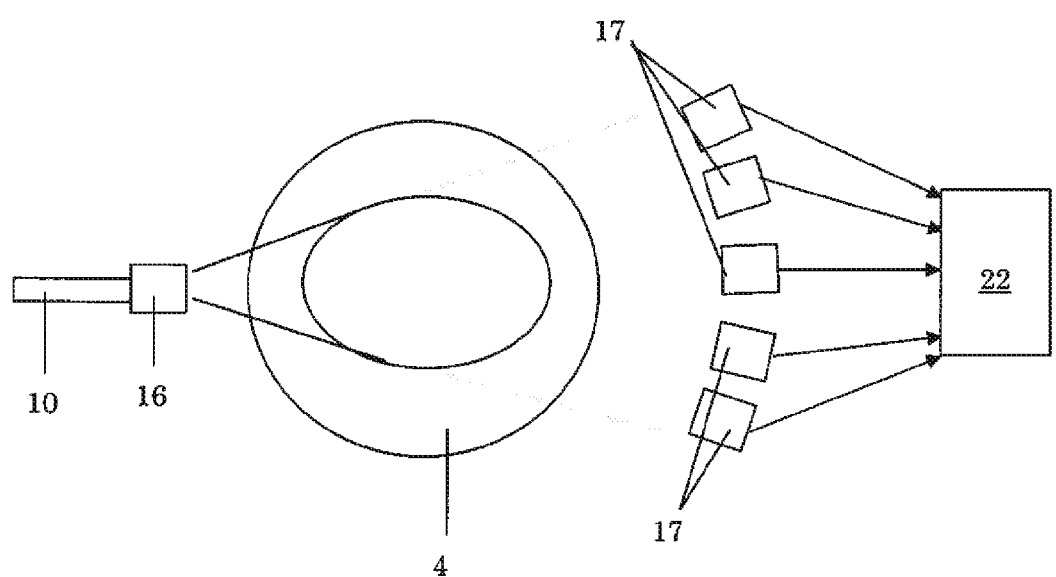
FIG. 8 depicts a top view of the embodiment of FIG. 7.

As illustrated in FIG. 6, the test surface 4 is provided in or near the focal plain of the collimating lens 18, so that the beam 3 after the lens 18 is parallel. The micro lens array 19 accordingly focuses at the mirror 20. The mirror 20 reflects the received light back into the direction where it came from. An potential advantage of a retro reflector 15, in particular of the displayed type, is that it makes the set-up tolerant for small position variations, especially in the presence of a curved test surface 4. In addition, in contrast to for example a corner cube type retroreflector, the polarization state of the light is substantially unaffected, which may improve the sensor performance of the beam for the prescribed minimal transmission wavelength. In addition, the embodiment of FIG. 6 may have a better light yield compared to other single retroreflector types. FIG. 7 shows an alternative ellipsometric setup for application in a EUV lithographic apparatus, and FIG. 8 shows a top view of the embodiment of FIG. 7. The light source 10 is mounted in vacuum, or the light may be coupled inside the vacuum chamber via optical fibers. The beam enters the polarized state generator (PSG) 16, where it is polarized (45 degrees) and modulated by a photo elastic modulator (PEM). Then beam 2 then strikes the test surface 4, which in this embodiment is an optical element (most sensitive around the Brewster's angle) and is reflected with a change in optical ellipse, represented by the reflected beam 3. The light is detected via a polarization state detector sensor (PSDS) 17, which includes a polarization state detector (PSD), a detector, and amplifier. The signals are transported outside the vacuum chamber, where a change in optical ellipse can be calculated in Δ, Ψ by a processor 22 (shown in FIG. 8). As shown in FIG. 8, there can be multiple polarization state detector sensors 17 for spatial information on each optical mirror. With the shift in Δ, an estimation of the EUV grown carbon can be measured and reproduced at sub-angstrom level, even by applying a single wavelength of the probing beam (2,3).

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

In addition, where in the application 'minimal transmission' is used, this is meant to encompass transmissions of certain range around null, in particular, a null transmission wavelength, where zero or close to zero light is transmitted through the polarization conditioning system. Furthermore, where in FIG. 2, the light source 10 and the spectral analyzer 12 are depicted outside the vessel, the invention is meant to encompass all embodiments wherein the test surface is partly or completely provided in a vessel, in particular, a vacuum environment. Furthermore, wherever in the description a 'test surface' is referenced, this may be an additional surface, which is not actively used as a reflective surface in the system. On the other hand, the test surface may be part of the active reflective surfaces of the system. The broadband light source is formed, for example, by a multispectral light source emitting a plurality of wavelengths at the same time, in other examples, it may be a light source emitting a single wavelength that may be varied, also called a tunable wavelength source. In case of a tunable wavelength source, the spectral analyzer 12 may be formed by a photo-detector. Furthermore a polarization filter can be formed by any optical polarization filter system known in the field, such as a Glan Thompson filters, Brewster filters, grid polarizers etc. The polarization filter may be incorporated in the spectral analyzer.

The descriptions above are intended to be illustrative, not limiting. Thus, it will be apparent to one skilled in the art that modifications may be made to the invention as described without departing from the scope of the claims set out below.

What is claimed is:

1. A lithographic apparatus comprising:
a vessel enclosing a component with a test surface to be probed for contamination control; and
an optical probe configured to transmit and receive an optical probing beam,
the vessel comprising a first optical port configured to transfer the optical probing beam towards the test surface, and a second optical port configured to receive a reflected optical probing beam,
the optical probe comprising a light source configured to provide the optical probing beam, a polarization conditioner configured to provide a predefined polarization state to the probing beam, and a spectral analyzer,
the polarization conditioner being preset to provide a minimal transmission for a minimal transmission wavelength, and the spectral analyzer being arranged to detect a wavelength shift of the minimal transmission wavelength in response to a polarization change due to the presence of contamination.

2. A lithographic apparatus according to claim 1, wherein the vessel is a vacuum vessel, and wherein the component is a projection mirror optic or an illumination mirror optic.

3. A lithographic apparatus according to claim 1, wherein the vessel comprises a single optical port, and a retroreflective element is arranged in a beam path of the probing beam, the retroreflective element being positioned to direct the reflected probing beam via the test surface from and to the single optical port.

4. A lithographic apparatus according to claim 1, wherein the retroreflective element comprises a collimating lens, a micro lens array, and a mirror.

5. A lithographic apparatus according to claim 4, wherein the test surface is provided in or near the focal plane of the collimating lens so that the probing beam is parallel after the collimating lens.

6. A lithographic apparatus according to claim 1, wherein the spectral analyzer is arranged with minimum identifying circuitry configured to identify a local minimum in the received wavelength spectrum; and a memory configured to associate a local minimum shift to a contamination level.

7. A lithographic apparatus according to claim 1, wherein the polarization conditioner comprises a polarizer and a retarder.

8. A lithographic apparatus according to claim 1, wherein the polarization conditioner is provided, in an optical path from the broadband light source, with a polarizer and a retarder, and wherein in an optical path from the test surface a polarization filter is arranged before the spectral analyzer.

9. A lithographic apparatus according to claim 1, wherein the polarization conditioner is provided within the vessel.

10. A vessel enclosing a component with a test surface to be probed for material deposition control, and an optical probe configured to transmit and receive an optical probing beam,
the vessel comprising a first optical port configured to transfer the probing beam towards the test surface, and a second optical port configured to receive a reflected probing beam, and
the optical probe comprising a broadband light source configured to provide the probing beam, a polarization conditioner to provide a predefined polarization state to the probing beam, a polarization filter, and a spectral analyzer, the polarization conditioner and polarization filter being preset to provide a null transmission for a predefined minimal transmission wavelength, and the spectral analyzer being arranged to detect a wavelength shift of the minimal transmission wavelength in response to a polarization change due to the presence of contamination.

11. A contamination monitoring method for monitoring contamination of a test surface enclosed in a vessel, the method comprising:
   transmitting an optical probing beam into the vessel;
   conditioning the optical probing beam to provide a minimal transmission after reflection on the test surface for a predefined minimal transmission wavelength and polarization state;
   receiving a reflected optical probing beam from the vessel into a spectral analyzer; and
   detecting a wavelength shift of the minimal transmission wavelength in response to a polarization change due to the presence of contamination with the spectral analyzer.

12. A contamination monitoring method according to claim 11, wherein the vessel is a vacuum vessel comprising a single optical port; the wherein method further comprises retroreflecting the probing beam to direct the reflected optical probing beam via the test surface from and to the optical port.

13. A contamination monitoring method according to claim 11, wherein the optical probing beam is a broadband light beam.

14. A lithographic apparatus according to claim 1, further comprising:
   an illumination system configured to condition a beam of radiation;
   a support configured to support a patterning device, the pattering device being configured to pattern the beam of radiation; and
   a projection system configured to project the patterned beam of radiation onto a substrate,
   wherein the component is located in the illumination system or the projection system.

15. A vessel according to claim 10, wherein the vessel comprises a single optical port, and wherein the vessel comprises a retroreflective element configured to be put in the beam path of the probing beam, the retroreflective element being aligned to direct the reflected probing beam via the test surface from and to the optical port.

* * * * *